United States Patent [19]

Frigerio et al.

[11] Patent Number: 5,510,538

[45] Date of Patent: Apr. 23, 1996

[54] PROCESS FOR THE OXIDATION OF PRIMARY AND SECONDARY ALCOHOLS TO ALDEHYDES AND KETONES AND FOR THE OXIDATION OF 1,2-DIOLS TO ALPHA-KETOLS AND ALPHA-DIKETONES

[75] Inventors: Marco Frigerio; Simona Sputore, both of Milan; Marco Santagostino, Magenta, all of Italy

[73] Assignee: SIGMA-TAU Industrie Farmaceutiche Riunite S.p.A., Rome, Italy

[21] Appl. No.: 356,971

[22] Filed: Dec. 16, 1994

[30] Foreign Application Priority Data

Dec. 16, 1993 [DE] Germany .......................... 43 43 054.6
Sep. 22, 1994 [IT] Italy ............................... RM94A0604

[51] Int. Cl.$^6$ ................................. C07C 45/29
[52] U.S. Cl. .......................... 568/347; 568/426; 568/420; 568/404; 568/41; 549/498; 549/398; 549/32; 546/301; 552/544; 552/576; 548/494; 564/343; 564/453

[58] Field of Search ....................... 568/322, 361, 568/404, 426, 41, 420, 404, 347; 549/498, 398, 32; 546/301; 552/544, 576; 548/498; 564/343, 453

[56] References Cited

PUBLICATIONS

Barton et al, Tetrahedron Letters, vol. 23, pp. 957–960 (1982).
Dess et al, J. Org. Chem., vol. 48, pp. 4155–4156 (1983).
Dess et al, J.A.C.S., vol. 113, pp. 7277–7287 (1991).

*Primary Examiner*—James H. Reamer
*Attorney, Agent, or Firm*—Oblon, Spivak, McClelland, Maier & Neustadt

[57] ABSTRACT

A process for the selective oxidation of a primary or secondary alcohol to an aldehyde or ketone and for the oxidation of a 1,2-diol to an α-ketol or α-diketone, which comprises contacting the alcohol or 1,2-diol with o-iodoxybenzoic acid. This process is suited for selective oxidation of alcohols containing easily oxidizable groups, such as amino or thioether groups and easily oxidizable heterocycles.

5 Claims, No Drawings

PROCESS FOR THE OXIDATION OF PRIMARY AND SECONDARY ALCOHOLS TO ALDEHYDES AND KETONES AND FOR THE OXIDATION OF 1,2-DIOLS TO ALPHA-KETOLS AND ALPHA-DIKETONES

The present invention relates to a process for the oxidation of a primary or secondary alcohols to aldehydes or ketones, respectively, and for the oxidation of 1,2-diols to a-ketols or α-diketones.

According to a further embodiment of the present invention, this process is also suited for selectively oxidizing to aldehydes or ketones primary or secondary alcohols containing other easily oxidizable groups, such as amino or thioether groups and easily oxidizable heterocycles, which remain wholly unchanged throughout the oxidation process.

The oxidation of alcoholic group to aldehyde and ketone is a useful reaction in organic chemistry and several methods are known, covering a variety of experimental conditions (general reference: J. March *Advanced Organic Chemistry* 4° Ed., J. Wiley 1992, pg. 1159– 1205). The most widely utilised oxidants are $CrO_3$ and $KMnO_4$, which, however, present serious drawbacks. Oxidations with $CrO_3$ are performed in a highly acidic medium, thus acid sensitive compounds can not be oxidized by this reagent. Moreover the isolation of the oxidized products from the soluble chromium-containing by-products brings about complex problems and usually a chromatographic method is necessary to make sure that the desired oxidized products are free of chromium pollutants.

$KMnO_4$ oxidations are mainly performed in a basic medium, thus base sensitive compounds can not be oxidized by this reagent. Moreover $KMnO_4$ oxidations must be performed at a temperature above room temperature (from 50° to 80° C.), thus preventing the use of $KMnO_4$ for selective oxidation of polifunctionals substrates.

In particular, both $CrO_3$ and $KMnO_4$ are not suitable for the oxidation of 1,2-diols because, instead of oxidizing them to α-ketols or α-diketones, they mainly, if not exclusively, cause the cleavage of the C—C bond (J. March, loc. cit. 1174; Corey E. J. and Kim C. U., *Tetrahedron Lett.* 1974, 287 and references therein cited).

Indeed few methods are available for the oxidation of 1,2-diols to α-ketols or α-diketones, and all suffer from serious drawbacks.

For example, same methods require rigorously anhydrous reaction conditions (Corey E. J. and Kim C. U. loc. cit.; Schobert R. *Synthesis* 1987, 741; Christi M. and Kraft A., *Angew. Chem. Int. Ed. Engl.* 1988, 27, 1369; Magnus P., Mendoza J. S., Stamford A., Ladlow M., Willis P. *J. Am. Chem. Soc.* 1992, 114, 10232), while other use expensive oxidants such as silver salts (Fetizori M., Golfier M. Louis J-M., Mourges P., *Tetrahedron Lett.* 1972, 4445) or 1-hydroxy-1,3 -dihydro-3,3-bis(trifluoromethyl)-1,2-benzoiodoxol 1-oxide (Grieco P. A., Collins J. L., Moher E. D., Fleck T. J., Gross R. S. *J. Am. Chem. Soc.* 1993, 6078).

Other methods use unselective oxidants such as dimethyldioxirane or methyl(trifluoromethyl)dioxirane (Murray R. W. and Jeyaraman R. *J. Org. Chem.* 1985, 2847; D'Accolti L., Detomaso A., Fusco C., Rosa A., Curci R. *J. Org. Chem.* 1993, 3600), or reagents such as organostannanes difficult to separate from organic products (Dailey O. D. and Fuchs P. L., *J. Org. Chem.*, 1980, 223).

Both the oxidation of an alcohol to an aldehyde or ketone as well as the oxidation of a vicinal diol to an α-ketol or a α-diketone are processes useful in the chemical industry.

For the sake of brevity it is not worth mentioning specific examples of oxidation of mono-hydroxy compounds to aldehyde or ketone derivatives due to the large number of known processes, used in any kind of chemically based industry, ranging from the petrol to the cosmetic industry. As regards some examples in the pharmaceutical field see e.g. A. Kleemann "Pharmazeutische Wirkstoffe" G. Thieme Verlag 1978.

As an example of oxidation of a 1,2-diol to α-ketol in the pharmaceutical field, see the Upjohn's cortisone synthesis ("Pharmazeutische Wirkstoffe", pg. 119, G. Thieme Verlag 1978).

The synthesis of gibberellic acid, which is used in the agrochemical industry, comprises the oxidation of 1,2-diol to α-ketol (E. J. Corey and Xue-Min Cheng, "The logic of chemical synthesis" pg. 206, J. Wiley & Sons 1989). Also the synthesis of the antitumoral alkaloid vinblastine and analogues thereof, reported by Magnus (Magnus P. et al. loc. cit.), involves the oxidation of an 1,2-diol to α-ketol.

Also in the foregoing industrial oxidation processes the same oxidants as those previously mentioned are the most frequently utilized and, therefore, substantially present the same aforesaid serious drawbacks.

The aforesaid, known oxidants bring about further serious drawbacks if the primary or secondary alcohol to be selectively oxidized to aldehyde or ketone, respectively, contain other easily oxidizable groups, such as amino and thioether groups and easily oxidizable heterocycles.

Both $CrO_3$ and $KMnO_4$ are unselective oxidants, thus it is impossible to oxidize selectively an alcohol in the presence of other easily oxidizable groups, such as amino and thioether groups and easily oxidizable heterocycles (N. L. Allinger, M. P. Cava, D. C. De Jongh, C. R. Johnson, N. A. Lebel and C. Stevens *Organic chemistry*, Worth Publisher, New York 1971, pages 575–576 and 683–686; T. L. Gilchrist, *Heterocyclic Chemistry*, Pitman Publishing Ltd. 1985, pages 126–185).

Indeed it is well known in the art, that oxidation processes performed in the presence of amino derivative lead to complex reaction mixtures whose nature depends on the particular experimental conditions used (such as for example solvent and temperature).

The oxidation of an amino-alcohol to an amino-aldehyde or aminoketone rarely possess a preparative usefulness (J. March loc. cit.; L. F. Fieser and M. Fieser *Reagents for organic Synthesis* Vol I, Wiley Eds. 1967, pages 142–147 and 942–952). Usually the protection of the amino group is required before the oxidation of the alcoholic group (T. W. Greene and P. G. M. Wuts, *Protective groups in organic synthesis*, Wiley Eds. 1991, pages 309–405).

Nitrogen containing heterocycles, such as for example pyrroles and indoles are easily oxidized by air and by a wide variety of oxidants (T. L. Gilchrist, loc. cit., page 170) and thus the heterocyclic nitrogen must be protected if one have to oxidize an alcoholic group present in the molecule (T. W. Greene and P. G. M. Wuts, loc. cit., pages 385– 397).

The overall synthetic process is thus extended by two reactions (protection and deprotection), lowering the final yield and lengthening the global reaction times.

Thioethers are quite easily oxidized to sulphoxide or sulphones, (N. L. Allinger and al. loc. cit.; T. W. Greene and P. G. M. Wuts, *Protective groups in organic synthesis*, Wiley Eds. 1991, page 439) and as they cannot be protected, thus the oxidation of an alcohol to an aldehyde or a ketone in the presence of a thioether group is a general synthetic problem.

We have now found that all the aforesaid drawbacks of the known oxidation methods and processes can be successfully overcome by the process of the present invention wherein o-iodoxybenzoic acid I is used as oxidizing agent.

O-iodoxybenzoic acid is represented by the following tautomeric equilibrium:

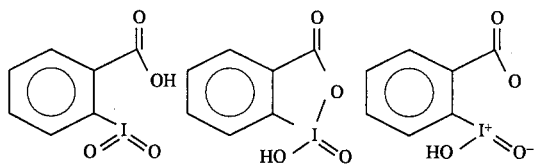

Therefore, the present invention provides a process for the oxidation of a primary or secondary alcohols which may further contain other oxidizable groups or heterocycles to an aldehyde or a ketone, respectively, and for the oxidation of a 1,2-diol to α-ketols or α-diketone, which comprises contacting the alcohol or 1,2-diol with o-iodoxybenzoic acid.

o-Iodoxybenzoic acid is a known compound, which was first prepared by Hartman and Meyer in 1893, (Chem. Ber. 1893, 26, 1727).

o-Iodoxybenzoic acid can be easily prepared from inexpensive starting materials, i.e. o-iodobenzoic acid and potassium bromate (see: Dess B. D. and Martin J. C., *J. Org. Chem.*, 1983, 4155).

Previous utilisation of o-iodoxybenzic acid and salts thereof are already known. Aqueous solutions of the potassium salt of I (potassium o-iodoxybenzoate) have been used in analytical chemistry for redox titration (Verna K. K. and Gulati A. K., *Anal. Chem.* 1982, 54, 2550; Verna K. K. and Tyagi P., *Anal. Chem.* 1984, 56, 2157; Verna K. K., Jain A., Stewart, K. K., *Anal. Chem. Acta,* 1992, 261).

Aqueous solutions of the sodium salt of I (sodium o-iodoxybenzoate) have been claimed as enhancers in photographic colour development, being cheaper and possessing fewer environmental problems than the usual ones (DE 2,657,438).

o-Iodoxybenzoic acid has been utilised for the preparation of Dess-Martin periodinane (1,1,1-triacetoxy-1,1-dihydro-1,2 -benzo-iodoxol-3(1H)-one) (Dess B. D. and Martin J. C., loc. cit. 1983).

However, to date o-iodoxybenzoic acid has never been used as an oxidant in any organic synthesis, probably because its "virtual insolubility in common organic solvents has discouraged the study of its chemical properties" (Dess B. D. and Martin J. C., loc. cit., 1991):

The discovery that o-iodoxybenzoic acid I oxidizes primary and secondary alcohols to aldehydes and ketones and 1,2-diols to α-ketols and α-diketones in mild conditions is unexpected for many reasons.

First, D. Barton and co-workers (Barton D. H. R., Godfrey C. R. A., Morzycki J. W., Mortherwell W. B., Stobie A., *Tetrahedron Lett.* 1982, 957) reported that the closely related compounds iodoxybenzene and m-iodoxybenzoic acid:

a) oxidize benzyl alcohols to benzaldehydes only at high temperature (80° C.), and b) cleave the C—C bond of 1,2-diols readily at room temperature. Secondly, it is well known that both inorganic and organic iododerivatives (NaIO$_4$, HIO$_4$, I(OAc)$_3$, I$_2$/HgO, Dess-Martin periodinane, phenyliodoso diacetate, iodoxybenzene, m-iodoxybenzoic acid) are the reagents of choice for the cleavage of the C—C bond of 1,2-diols and α-ketols.

It is thus surprising that o-iodoxybenzoic acid:

a) selectively oxidizes primary alcohols to aldehydes and secondary alcohols to ketones at room temperature without oxidizing other easily oxidizable groups, if any;

b) does not cleave the C—C bond of 1,2-diols, but oxidizes them to αketols and α-diketones; and c) does not cleave the C—C bond of α-aminoalcohols and oxidizes them to α-aminoaldehydes and α-aminoketones.

This is particularly surprising since we have found that o-iodoxybenzoic acid salts such as tetrabutylammonium o-iodoxybenzoate and 7-methyl-1,5,7-triazabicyclo[4.4.0]-dec-5-ene o-iodoxybenzoate salt do cleave the C—C bond of 1,2-diols, as would be normally expected with iodo-containing oxidants.

Thus, the oxidizing behaviour of o-iodoxybenzoic acid is surprising because it not only differs from that of its close analogues (iodoxybenzene and m-iodoxybenzoic acid) but also from that of its own salts.

Finally we have found that o-iodoxybenzoic acid dissolves readily in DMSO, (up to 420 g/l (1.5M) at 20° C.), contrary to literature reports (Katritsky A. R., Duell B. L., Gallos J. K., *Org. Magn. Reson.*, 1989, 27, 1007; Katritsky A. R., Savage G. P., Gallos J. K., Dupont Durst H., *J. Chem. Soc., Perkin Trans* 2, 1990, 1515; Dess B. D. and Martin J. C., loc. cit.; 1991)

The oxidation is most preferably carried out in a dimethylsulfoxide (DMSO) containing reaction medium. Optionally a cosolvent (as herein below defined) may be present. The oxidation shall be carried out at a temperature from −40° to 60° C., preferably at room temperature, with reaction times ranging from few minutes to 48 hrs, usually from 1 to 48 hrs.

The amount of o-iodoxybenzoic acid may vary from one mole to several moles (e.g. 6–10 moles) per mole of oxidizable alcoholic group. The use of several moles of o-iodoxybenzoic acid per oxidizable alcoholic group merely accelerate the kinetic of the oxidation process without modifying the nature of the final products. Thus, e.g. primary alcohols are oxidized to aldehydes both with one mole and ten moles of o-iodoxybenzoic acid, and in neither case primary alcohols are oxidized to the corresponding carboxylic acids.

O-iodoxybenzoic acid-oxidizes selectively the alcoholic group to aldehyde or ketone, without oxidizing the amino and thioether groups or oxidizable heterocycle present in the molecule, the selectivity of the process being independent on the amount of o-iodoxybenzoic add used, i.e. no oxidation of amino or thioether or heterocycle is detected using several moles of o-iodoxybenzoic acid.

The oxidation of amino-alcohols is preferably performed in the presence of an acid such as acetic acid or trifluoroacetic add in order to decrease the reaction times.

According to a first embodiment of the oxidation process of the present invention, o-iodoxybenzoic acid is dissolved in DMSO and to the resulting solution the alcohol or 1,2-diol is then added, either as a solid, as a liquid or dissolved in an organic cosolvent such as, for example, DMSO, sulfolane, N,N-dimethylformamide (DMF), N-methylpyrrolidone. hexamethyl-phosphoramide (HMPA), hexamethylphosphorous triamide (HMPT), acetonitrile, chloroform, dichloromethane, acetone, tetrahydrofurane (THF), dioxane, diethyl ether, hexane, benzene, pyridine, acetic acid, trifluoracetic acid, ethylacetate and water or their mixtures.

According to a second embodiment, the addition of the reagents is reversed in order, i.e. first the alcohol or the 1,2-diol is dissolved in one of the above mentioned cosolvents or in a mixture of them, then o-iodoxybenzoic acid is added either as a solid or in DMSO solution, provided that when o-iodoxybenzoic acid is added as a solid, then the alcohol or the 1,2-diol is dissolved in DMSO or in a mixture of DMSO with one of the above listed cosolvents.

According to a further embodiment of the present invention, a slurry of o-iodoxybenzoic acid in DMSO, optionally in the presence of a cosolvent, can be used.

A suitable cosolvent-that can be mixed with a slurry of o-iodoxybenzoic acid in DMSO is everyone of the above listed cosolvents. Mixtures of these cosolvents can also be used.

The oxidation of primary and secondary alcohols to aldehydes and ketones and the oxidation of 1,2-diols to α-ketols and α-diketones by the use of slurry of o-iodoxybenzoic acid in DMSO is performed analogously to the oxidation with o-iodoxybenzoic acid DMSO solution, i.e. suspending o-iodoxybenzoic acid in DMSO, optionally in the presence of a cosolvent, and adding de alcohol or the 1,2-diol, or if preferred dissolving the alcohol or 1,2-diol in DMSO, optionally in the presence of a cosolvent, and then adding the solid o-iodoxybenzoic acid in one or more portions.

The work-up is easily performed by dilution of the reaction mixture with water, filtration of the white precipitate and extraction of the obtained aldehydes, ketones, α-ketols and α-diketones with a suitable organic solvent, such as for example chloroform, dichloromethane, diethyl ether, hexane, benzene or ethyl acetate. The organic and water layer are separated, the organic extracts are dried over a suitable dessicant (such as for example sodium and magnesium sulfate) and the solution evaporated to dryness under vacuum. Purification of the obtained products is performed by standard procedure such as crystallisation, distillation or chromatography.

If desired, filtering off the white precipitate from the reaction mixture can be substituted by washing the organic layers with a base, such as sodium or potassium bicarbonate, sodium or potassium carbonate or ammonium hydroxide and the products isolated as above described.

o-Iodoxybenzoic acid was prepared as follow:

Preparation of o-iodoxybenzoic Acid I.

o-Iodoxybenzoic acid I was prepared according to Dess-Martin procedure (Dess D. B. and Martin J. C.. loc. cit., 1991), but after the water washing, it was rinsed with anhydrous acetone instead of ethanol.

A suspension of 2-iodobenzoic acid (8.52 g, 34 mmol) in $H_2SO_4$ (0.73M, 73 ml) was vigorously stirred at 55° C. $KBrO_3$ (7.6 g 45 mmol) was added in portions during 30 minutes. The orange suspension was heated at 68° C. for 3 hr and 45 minutes then it was cooled to 0° C. and the solid precipitate was filtered. The solid was washed on the filter with water (7×20 ml), acetone (2×10 ml) and diethyl ether (7×20 ml) to give 9.05 g (94%) of o-iodoxybenzoic acid I, m.p. 226°–234° C.

IR (film) 1640 cm$^{-1}$ $^1$H-NMR (DMSO-d$_6$): 8.15 (1H, d), 8.01 (1H, d), 7.98 (1H, t), 7.84 (1H, t). $^{-}$C-NMR (DMSO-d$_6$):167.49, 146.59, 133.39, 132.97, 131.36, 130.10, 124.99.

Anal. for $C_7H_5IO_4$:
Calcd.: C, 30.30; H, 1.80; I, 45.32.
Found: C, 30.13; H, 1.75; I, 45.05.

The following examples illustrate the invention without limiting it.

EXAMPLE 1

Oxidation of benzyl alcohol to benzaldehyde.

o-Iodoxybenzoic acid I (2.90 g; 10.36 mmol) was added under stirring to a solution of benzyl alcohol (ml 0.96; mmol 9.35) in DMSO (10 ml). The slurry-thus obtained dissolves in 5 min with spontaneous heating. The reaction temperature was controlled by an ice-water bath not to rise above 40° C. After 15 min the reaction was diluted with water (20 ml) and diethyl ether (20 ml). The reaction mixture was filtered, the white precipitate washed with diethyl ether, the aqueous solution extracted with diethyl ether (3×10 ml). The combined organic layers were washed with a 5% aqueous solution of $NaHCO_3$ (3×5 ml) and dried over sodium sulfate. The organic solvent was distilled under vacuum in a Vigreux apparatus and g 0.96 (97%) of benzaldehyde (boiling at 60°–62° C./10 mm). were collected.

The $^1$-NMR spectrum was identical to that of an authentic sample.

EXAMPLE 2

Oxidation of (–)-borneol to (–)-camphor. o-Iodoxybenzoic acid I (123 mg; 0.44 mmol) was added in one portion under stirring to a solution of (–)-borneol (62 mg; 0.40 mmol) in DMSO (1 ml). The slurry thus obtained dissolved immediately. After 2.5 h the reaction mixture was poured into a 10% aqueous solution of $Na_2CO_3$. The reaction mixture was filtered, the white precipitate washed with diethyl ether, the aqueous solution extracted with diethyl ether (3×5 ml). The combined organic layers were washed with brine and dried over sodium sulfate. The organic solvent was distilled under vacuum and the residue was sublimed to give 61 mg (100% ) of (–)-camphor, mp 179°–180° C.

The $^1$-NMR spectrum was identical to that of an authentic sample.

EXAMPLE 3–10

Using the procedure described in Example 2, the compounds listed in following Table 1 were prepared.

TABLE 1

| Ex. n° | Alcohol | Carbonyl derivative | Yield$^a$ % | Time min |
|---|---|---|---|---|
| 3 | (structure with OH) | (structure with =O) | 100 | 150 |

TABLE 1-continued

| Ex. n° | Alcohol | Carbonyl derivative | Yield[a] % | Time min |
|---|---|---|---|---|
| 4 | (bornyl-type alcohol structure) | (camphor-type ketone structure) | 90 | 45 |
| 5 | (isoborneol-type alcohol structure) | (camphor-type ketone structure) | 95 | 15 |
| 6 | (pinene-ethanol structure with OH) | (pinene-acetaldehyde structure) | 91 | 270 |
| 7 | (furfuryl alcohol) | (furfural) | 88 | 40 |
| 8 | (3-pyridinyl methanol) | (3-pyridinecarboxaldehyde) | 99 | 15 |
| 9 | (phenethyl alcohol) | (phenylacetaldehyde) | 82 | 60 |
| 10 | (1,1-bis(hydroxymethyl)cyclohex-3-ene) | (1,1-diformyl cyclohex-3-ene) | 98 | 120[b] |

[a]: yields of isolated compounds (flash chromatography or crystallisation).
[b]: 2.2 mol of o-iodoxybenzoic acid were used (i.e. 1.1 mols per oxidizable alcoholic group).

EXAMPLE 11

Oxidation of digitoxigenin to 14 β-hydroxy-5β-card-20(22)enolid-3-one.

Digitoxigenin (mg 380, 1.01 mmol) was added to a solution of o-iodoxybenzoic acid I (550 mg, 1.96 mmol) in DMSO (7 ml). After 3 hours the solution was diluted with NaHCO₃ (2.5%, 30 ml) and extracted with ethyl acetate (3×10 ml). The combined organic layers were washed with water (2×5 ml), dried over sodium sulfate and evaporated to dryness under vacuum. The residue was triturated with ethyl acetate to give 350 mg (92%) of 14β-hydroxy-5β -card-20(22)enolid-3-one mp 201°–204° C. (lit. 234°–235° C.: Beilsteins Handbuch der organischen Chemie, V E., 18/3, 506)

EXAMPLE 12

Oxidation of dihydrocholesterol to 5α-cholestan-3-one.

A solution of dihydrocholesterol (1.94 g; 5 mmol) in THF (8 ml) was added to a solution of o-iodoxybenzoic acid I (2.10 g, 7.5 mmol) in DMSO (14 ml). After 2 hr precipitation of a white solid was observed. After 5 hr the reaction solution was poured into Na₂CO₃ (5%, 40 ml) and extracted with diethyl ether/n-hexane (50:50; 3×30 ml). The combined organic layers were washed with water (2×15 ml), dried over sodium sulfate and brought to dryness under vacuum. The residue was crystallised from ethanol to give 1.73 g (89%) of 5α -cholestan-3-one mp 129°–130° C. (lit. 128°–130° C.: Beilsteins Handbuch der organischen Chemie, III E., 7, 1330b).

EXAMPLES 13 AND 14

Using the procedure described in Example 12, the compounds listed in the following Table 2 were prepared:

TABLE 2

| Ex. n° | Alcohol | Ketone | Yield[a] % | Oxidant equiv. | Time hours |
|---|---|---|---|---|---|
| 13 | (cholesterol structure, HO-) | (cholest-4-en-3-one structure, O=) | 75 | 6 | 2 |
| 14 | (hydroxy-steroid ketone, HO-) | (dione structure, O=) | 78 | 10 | 1 |

[a]: yields of isolated compounds (flash chromatography).

EXAMPLE 15

Oxidation of 18β-glycyrrhetinic acid to 3,11-dioxo-olean-12-en-30 acid.

o-Iodoxybenzoic acid I (42 mg, 0,15 mmol) was added to a solution of 18β-glycyrrhetinic acid (47 mg; 0.1 mmol) in DMSO (0,34 ml) at room temperature. After 4 hr the reaction solution was diluted with water (5 ml) and diethyl ether (10 ml). The reaction mixture was filtered; the layers were separated and the aqueous solution was extracted with diethyl ether (2×5 ml). The combined organic layers were washed with water (2×10 ml), dried over sodium sulfate and evaporated to dryness under vacuum. The residue was triturated with methanol to give 42 mg (90%) of 3,11-dioxo-olean-12-en-30 acid mp>280° C. (lit. 295° C., Bellsteins Handbuch der organischen Chemie, IV E., 10, 3186)

EXAMPLE 16

Oxidation of Meso-Hydrobenzoin to Benzil.

meso-Hydrobenzoin (mg 250, 1.17 mmol) was added to a solution of o-iodoxybenzoic acid I (820 mg, 2.93 mmol) in DMSO (15 ml). After 2 hours the solution was diluted with water, filtered and extracted with diethyl ether (3×15 ml). The combined organic layers were washed with water (2×5 ml), dried over sodium sulfate and evaporated to dryness under vacuum. The residue was triturated with n-hexane to give 228 mg (93%) of benzil, mp 91°–94° C. (lit. 94°–95° C.)

EXAMPLES 17–19

Oxidation of the 1,2-diols listed in Table 3, with o-iodoxybenzoic acid, according to the procedure described in Example 16, gave the diketones shown:

TABLE 3

| Ex. n° | 1,2-Diol | 1.2-diketone | Yield[a] % | Time hours |
|---|---|---|---|---|
| 17 | HO-CH(CH3)-CH(CH3)-OH | O=C(CH3)-C(CH3)=O | 100[b] | 3 |
| 18 | cis-cyclohexane-1,2-diol | cyclohexane-1,2-dione | 81 | 3,5 |
| 19 | trans-cyclohexane-1,2-diol | cyclohexane-1,2-dione | 78 | 5 |

[a]: yields of isolated compound.
[b]: yield determined by NMR spectroscopy.

EXAMPLE 20

Oxidation of 1,2-diphenyl-1,2-butanediol to 2-hydroxy-1,2-diphenyl-butan-1-one.

o-Iodoxybenzoic acid I (210 mg; 0.75 mmol) was added in one portion to a stirred solution of 1,2-diphenyl-1,2-butanediol (121 mg; 0.5 mmol) in DMSO (1.7 ml). After 1.5 h the reaction was poured in ml of a solution of $Na_2CO_3$ (10%) and extracted with diethyl ether (3×10 ml). The combined organic layers were washed with brine and dried over sodium sulfate. The Organic solvent was distilled under vacuum. The residue was triturated with n-pentane to give 120 mg (98%) of 2-hydroxy-1,2-diphenyl-butan-1-one mp 62°–68° C. (lit. 68°–69° C.: MacKenzie A. and Richtie A. Chem. Ber. 1937, 70, 23).

EXAMPLES 21 and 22

Oxidation with o-iodoxybenzoic acid of the secondary alcohol of the vicinal 1,2-diols listed in Table 4, according to procedure described in Example 20, gave the α-hydroxyketones shown:

TABLE 4

| Ex. n° | 1,2-Diol | Ketone | Yield[a] % | Oxidant equiv. | Time hours |
|---|---|---|---|---|---|
| 21 | | | 85[b] | 1.1 | 0,75 |
| 22 | | | 85[c] | 6 | 1 |

[a]: yields of isolated products (flash chromatography)
[b]: 10% of 3,6-diketone was also obtained
[c]: 15% of starting material was recovered

EXAMPLE 23

Oxidation of pinanediol to 2-hydroxy-3-pinanone.

o-Iodoxybenzoic acid I (420 mg; 1.5 mmol) was added under stirring in one portion to a solution of pinanediol (170 mg; 1 mmol) in DMSO (3.4 ml) and THF (2.9 ml) at 0° C. After 3 h the reaction was poured in 20 ml of a solution of Na₂CO₃ (10%) and extracted with diethyl ether (3×10 ml). The combined organic layers were dried over sodium sulfate. The organic solvent was distilled under vacuum. The residue was purified by chromatography (SiO₂, dichloromethane) to give after trituration with n-hexane, 145 mg (86%) of 2-hydroxy-pinanone, mp 30°–32° C.

EXAMPLE 24

Oxidation of 21-acetoxy-17,20-dihydroxy-pregn-4-en-3,11-dione to cortisone acetate.

A solution of 21-acetoxy-17,20-dihydroxy-pregn-4-en-3,11-dione (730 mg, 1.81 mmol) and o-iodoxybenzoic acid I (1 g, 3.57 mmol) in DMSO (7 ml) was stirred at 50° C. for 3 h. The solution was then diluted with water (10 ml), stirred for 10 min, filtered and extracted with ethyl acetate (3×10 ml). The combined organic layers were washed with brine and dried over sodium sulfate. The organic solvent was distilled under vacuum. The residue was crystallised from ethanol to give 676 mg (93%) of cortisone acetate, mp 238°–240° C. (lit. 238°–240° C.)

EXAMPLE 25

Oxidation of prednisone to 17α-hydroxy-21-al-1,4-pregnadien-3,11,20-trione

A solution of prednisone (100 mg, 0.27 mmol) and o-iodoxybenzoic-acid I (153 mg, 0.55 mmol) in DMSO (1.1 ml) was stirred at room temperature for 24 h. The solution was then diluted with water (5 ml), stirred for 10 min, filtered and extracted with dichloromethane (3×10 ml). The combined organic layers were washed with brine and dried over sodium sulfate. The Organic solvent was distilled under vacuum. The residue was triturated with acetone/water (50:50) to give 55 mg (52%) of 17α-hydroxy-21-al-1,4-pregnadien-3,11,20-trione hydrate mp 225°–229° C. (lit 230°–40° C. Herzog, H. L., Gentles M. J., Hershberg E. B. J. Org. Chem. 1956, 688).

EXAMPLE 26

Oxidation of thiochroman-4-ol to thiochroman-4-one.

o-Iodobenzoic acid I (980 mg; 3.50 mmol) was added under stirring to a solution of thiochroman-4-ol (500 mg; 2.92 mmol) in DMSO (8.8 ml). The slurry thus obtained dissolves in 15 min. After 24 h the reaction was diluted with water (20 ml) and diethyl ether (20 ml). The reaction mixture was filtered, the white precipitate washed with diethyl ether, the aqueous solution extracted with diethyl ether. (3× 10 ml). The combined organic layers were washed with a 5% aqueous solution of NaHCO₃ (3×5 ml) and dried over sodium sulfate. The organic solvent was distilled under vacuum in a Vigreux apparatus and 400 mg (92%) of thiochroman-4-one (boiling at 152°–156° C./12 mm) were collected.

The ¹-NMR spectrum was identical to that of an authentic sample.

EXAMPLES 27–30

Using the procedure described in Example 26, the compounds listed in the following Table 5 were prepared.

TABLE 5

| Ex. n° | Alcohol | Carbonyl derivative | Yield[a] % | Time h |
|---|---|---|---|---|
| 27 | HOCH2CH2-S-CH2CH2-S-CH2CH2OH structure | OHC-CH2-S-CH2CH2-S-CH2-CHO structure | 95[b] | 3 |
| 28 | dithiolane-spiro-cyclohexanol | dithiolane-spiro-cyclohexanone | 78 | 24 |
| 29 | PhCH2CONH-β-lactam-CH2OH with CO2CHPh2 | PhCH2CONH-β-lactam-CHO with CO2CHPh2 | 91 | 8 |
| 30 | Ph-CH(BocNH)-CONH-β-lactam-CH2OH with CO2CHPh2 | Ph-CH(BocNH)-CONH-β-lactam-CHO with CO2CHPh2 | 94 | 12 |

[a]: yields of isolated compounds (flash chromatography or crystallisation).
[b]: 2.2 mol of o-iodoxybenzoic acid were used (i.e. 1.1 mols per oxidizable alcoholic group).

EXAMPLE 31

Oxidation of N-Methylephedrine to 2-dimethyl-amino-1-phenyl-propan-1-one.

N-Methylephedrine (500 mg, 2.79 mmol) was added to a solution of o-iodoxybenzoic acid I (7.8 g; 27.9 mmol) in DMSO (55 ml). After 48 hours the solution was diluted with NaHCO$_3$ (2.5%, 30 ml) and extracted with ethyl acetate (3×10 ml). The combined organic layers were washed with water (2×5 ml), dried over sodium sulfate and evaporated to dryness under vacuum. The residue was purified by distillation to give 460 mg (92%) of 2-dimethylamino-1-phenyl-propan-1-one (boiling at 113°–117° C./12 mm).

The $^1$-NMR spectrum was identical to that of an authentic sample.

EXAMPLE 32

Oxidation of N-Methylephedrine to 2-dimethylamino-1-phenyl-propan-1-one in the presence of trifluoroacetic acid.

N-Methylephedrine (200 mg; 1.12 mmol) was added to a solution of o-iodoxybenzoic acid I (1.56 g, 5.59 mmol) and trifluoroacetic acid (0.13 ml) in DMSO (12 ml). After 8 hours the solution was diluted with NaHCO$_3$ (2.5%, 30 ml) and extracted with ethyl acetate (3×10 ml). The combined organic layers were washed with water (2×5 ml), dried over sodium sulfate and evaporated to dryness under vacuum to give 180 mg (90%) of 2-dimethylamino-1-phenyl-propan-1-one identical to the sample obtained in Example 31.

EXAMPLES 33–36

Using the procedure described in Example 31, the compounds listed in the following Table 6 were prepared.

TABLE 6

| Ex. n° | Alcohol | Ketone | Yield[a] % | Oxidant equiv. | Time hours |
|---|---|---|---|---|---|
| 33 | indole-2-CH2OH | indole-2-CHO | 89 | 1.5 | 8 |

TABLE 6-continued

| Ex. n° | Alcohol | Ketone | Yield[a] % | Oxidant equiv. | Time hours |
|---|---|---|---|---|---|
| 34 | 3-(hydroxymethyl)indole (CH$_2$OH) | indole-3-carbaldehyde (CHO) | 98 | 1.2 | 8 |
| 35 | 3-(2-hydroxyethyl)indole (CH$_2$CH$_2$OH) | 3-(indol-3-yl)acetaldehyde (CH$_2$CHO) | 79 | 1.2 | 6 |
| 36 | indole alkaloid with CH$_2$OH | indole alkaloid with CHO | 91 | 1.5 | 24 |

[a]: yields of isolated compounds (flash chromatography).

Examples 37–39

Using the procedure described in Example 32, the compounds listed in the following Table 7 were prepared.

TABLE 7

| Ex. n° | Alcohol | Ketone | Yield[a] % | Oxidant equiv. | Time hours |
|---|---|---|---|---|---|
| 37 | cyclohexanol with NH$_2$ substituent (OH) | cyclohexanone with NH$_2$ substituent (O) | 91 | 1.5 | 5 |
| 38 | 2-amino-1-phenylethanol (OH, NH$_2$) | 2-aminoacetophenone (O, NH$_2$) | 89 | 5 | 3.5 |
| 39 | 2-(methylamino)-1-phenylethanol (OH, NHMe) | 2-(methylamino)acetophenone (O, NHMe) | 85 | 2 | 24 |

[a]: yields of isolated compounds (flash chromatography).

We claim:

1. A process for the selective oxidation of a primary or secondary alcohol to an aldehyde or ketone and for the oxidation of a 1,2-diol to an α-ketol or α-diketone, which comprises contacting the alcohol or 1,2-diol with o-iodoxybenzoic acid in a DMSO-containing reaction medium.

2. The process of claim 1, wherein the oxidation is carried out at a temperature from −40° to 60° C., for a reaction time from a few minutes to 48 hours.

3. The process of claim 1, wherein the reaction medium further comprises a cosolvent.

4. The process of claim 3, wherein the cosolvent is selected from sulfolane, N,N-dimethylformamide, N-methylpyrrolidone, hexamethylphosphoramide, hexamethylphosphorous triamide, acetonitrile, chloroform, dichloromethane, acetone, tetrahydrofurane, dioxane, diethyl ether, hexane, benzene, pyridine, acetic acid, trifluoracetic acid, ethyl acetate and water or mixtures thereof.

5. The process of any one of the proceeding claims wherein the primary or secondary alcohol or the 1,2-diol further contain an amino group, a thioether group or an N-containing heterocycle.

* * * * *